US00PP27481P2

(12) United States Plant Patent
Dummen

(10) Patent No.: US PP27,481 P2
(45) Date of Patent: Dec. 20, 2016

(54) ***PHLOX* PLANT NAMED 'DUEPHLOIMDEBU'**

(50) Latin Name: *Phlox drummondii*
Varietal Denomination: Duephloimdebu

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 33 days.

(21) Appl. No.: 14/544,726

(22) Filed: Feb. 9, 2015

(51) Int. Cl.
*A01H 5/02* (2006.01)

(52) U.S. Cl.
USPC ..... Plt./320

(58) Field of Classification Search
USPC ..... Plt./263.1, 320
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Phlox* plant named 'Duepliloimdebu', characterized by its upright to outwardly spreading and mounding plant habit; medium in size; freely branching habit; freely and early flowering habit; and relatively large violet blue-colored flowers.

1 Drawing Sheet

Botanical designation: *Phlox drummondii.*
Cultivar denomination: 'DUEPHLOIMDEBU'.

BACKGROUND OF THE INVENTION

The present invention relates to a new and distinct cultivar of *Phlox* plant, botanically known as *Phlox drummondii* and hereinafter referred to by the name 'Duephloimdebu'.

The new *Phlox* plant is a product of a planned breeding program conducted by the Inventor in Rheinberg, Germany. The objective of the breeding program is to create new container-type *Phlox* plants with numerous attractive flowers.

The new *Phlox* plant originated from a cross-pollination conducted by the Inventor in Rheinberg, Germany in June, 2012 of a proprietary selection of *Phlox drummondii* identified as code number PH09-0503-003, not patented, as the female, or seed, parent with a proprietary selection of *Phlox drummondii* identified as code number PH09-0604-002, not patented, as the male, or pollen, parent. The new *Phlox* plant was discovered and selected by the Inventor as a single flowering plant within the progeny of the stated cross-pollination in a controlled greenhouse environment in Rheinberg, Germany in May, 2014.

Asexual reproduction of the new *Phlox* plant by cuttings in a controlled environment in Rheinberg, Germany since July, 2014 has shown that the unique features of this new *Phlox* plant are stable and reproduced true to type in successive generations.

SUMMARY OF THE INVENTION

Plants of the new *Phlox* plant have not been observed under all possible combinations of environmental and cultural conditions. The phenotype may vary somewhat with variations in environmental conditions such as temperature and light intensity without, however, any variance in genotype.

The following traits have been repeatedly observed and are determined to be the unique characteristics of 'Duephloimdebu'. These characteristics in combination distinguish 'Duephloimdebu' as a new and distinct *Phlox* plant:

1. Upright to outwardly spreading and mounding plant habit; medium in size.
2. Freely branching habit.
3. Freely and early flowering habit.
4. Relatively large violet blue-colored flowers.

Plants of the new *Phlox* can be compared to plants of the female parent selection. Plants of the new *Phlox* differ primarily from plants of the female parent selection in flower color as plants of the female parent selection have cream-colored-colored flowers. In addition, plants of the new *Phlox* are more compact than plants of the female parent selection.

Plants of the new *Phlox* can be compared to plants of the male parent selection. Plants of the new *Phlox* differ primarily from plants of the male parent selection in flower color as plants of the male parent selection have pinkish purple-colored flowers.

Plants of the new *Phlox* can be compared to plants of *Phlox drummondii* 'Duephlopusky', disclosed in U.S. Plant patent application Ser. No. 13/815,062, abandoned. In side-by-side comparisons, plants of the new *Phlox* and 'Duephlopusky' differed in the following characteristics:

1. Plants of the new *Phlox* were larger than plants of 'Duephlopusky'.
2. Plants of the new *Phlox* had smaller leaves than plants of 'Duephlopusky'.
3. Plants of the new *Phlox* were more freely flowering than plants of 'Duephlopusky'.
4. Plants of the new *Phlox* had larger flowers than plants of 'Duephlopusky'.
5. Plants of the new *Phlox* and 'Duephlopusky' differed in flower color as plants of 'Duephlopusky' had purple-colored flowers.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph comprises a side perspective view of a typical flowering plant of 'Duephloimdebu'.

DETAILED BOTANICAL DESCRIPTION

The aforementioned photograph and following observations, measurements and values describe plants grown during the summer in 12-cm containers in a glass-covered greenhouse in Rheinberg, Germany and under cultural practices typical of commercial production. During the production of the plants, day and night temperatures averaged 18° C. and light levels averaged 4,500 lux. Plants were pinched one time three weeks after planting and were 13 weeks old when the photograph and description were taken. In the following description, color references are made to The Royal Horticultural Society Colour Chart, 2001 Edition, except where general terms of ordinary dictionary significance are used.

Botanical classification: *Phlox drummondii* 'Duephloimdebu'.

Parentage:

*Female, or seed, parent*.—Proprietary selection of *Phlox drummondii* identified as code number PH09-0503-003, not patented.

*Male, or pollen, parent*.—Proprietary selection of *Phlox drummondii* identified as code number PH09-0604-002, not patented.

Propagation:

*Type*.—By cuttings.

*Time to initiate roots, summer*.—About five days at temperatures about 20° C.

*Time to initiate roots, winter*.—About seven days at temperatures about 20° C.

*Time to produce a rooted plant, summer*.—About three weeks at temperatures about 20° C.

*Time to produce a rooted plant, winter*.—About four weeks at temperatures about 20° C.

*Root description*.—Fine, fibrous; white in color.

*Rooting habit*.—Freely branching; dense.

Plant description:

*Plant and growth habit*.—Upright to outwardly spreading and mounding plant habit; broad inverted triangle; medium in size; low to moderately vigorous growth habit; freely branching habit with about five main laterals developing per plant with numerous secondary laterals; relatively short internodes; dense and bushy plant habit.

*Plant height*.—About 34 cm.

*Plant width* (*spread*).—About 85 cm.

*Lateral branches*.—Length: About 41.5 cm. Diameter: About 4.5 mm. Internode length: About 1.9 cm. Strength: Strong. Texture: Smooth, glabrous. Color: Close to 145B and 195B.

Leaf description:

*Arrangement*.—Opposite, simple.

*Length*.—About 3 cm.

*Width*.—About 9 mm.

*Shape*.—Elliptic.

*Apex*.—Apiculate.

*Base*.—Truncate to obtuse.

*Margin*.—Finely serrate; slightly revolute.

*Texture, upper and lower surfaces*.—Smooth, glabrous.

*Venation pattern*.—Pinnate.

*Color*.—Developing leaves, upper surface: Close to 137A. Developing leaves, lower surface: Close to 137C. Fully expanded leaves, upper surface: Close to 144A; venation, close to 145A. Fully expanded leaves, lower surface: Close to 144C; venation, close to 143D.

*Petioles*.—Length: About 1 mm. Diameter: About 1 mm. Texture, upper and lower surfaces: Smooth, glabrous. Color, upper and lower surfaces: Close to 144C.

Flower description:

*Flower type and flowering habit*.—Single rotate salverform flowers arranged in panicles; flowers face mostly upright to outwardly; freely flowering habit with about three to four flowers per inflorescence and about 2,600 flowers potentially developing per plant.

*Fragrance*.—Moderately fragrant; sweet, pleasant.

*Natural flowering season*.—Continuously flowering from summer to late summer in Germany; plants begin flowering about six weeks after planting.

*Postproduction longevity*.—Flowers last about three to four days on the plant; flowers not persistent.

*Flower buds*.—Height: About 1.4 cm. Diameter: About 3.6 mm. Shape: Narrowly obovate. Color: Close to 87B.

*Inflorescence height*.—About 3 cm.

*Inflorescence diameter*.—About 6.1 cm.

*Flower diameter*.—About 3.2 cm.

*Flower depth*.—About 2.6 cm.

*Flower throat diameter*.—About 2.9 mm.

*Flower tube length*.—About 1.5 cm.

*Flower tube diameter, at the base*.—About 2.6 mm.

*Petals*.—Quantity per flower and arrangement: Five petals in a single whorl and fused at the base into a narrow tube. Length from throat: About 1.7 cm. Width: About 1.5 cm. Shape: Spatulate. Apex: Rounded. Margin: Entire. Texture, petal lobes, upper and lower surfaces: Smooth, glabrous. Texture, throat and tube: Smooth, glabrous. Color: Developing petals, upper surface: Close to 81B and 82C. Developing petals, lower surface: Close to 85D and 87D. Fully expanded petals, upper surface: Close to 97C and 79B; venation, close to 85D; colors becoming closer to 97D and 90B with development. Fully expanded petals, lower surface: Close to 97D; venation, close to 97C. Flower throat: Close to 80A; venation, close to 79A. Flower tube: Close to 143D and 69A; venation, close to 59C.

*Sepals*.—Quantity per flower and arrangement: Five sepals in a single whorl and fused towards the base into a slender tube. Length: About 8.2 mm. Width: About 1.2 mm. Shape: Lanceolate. Apex: Narrowly apiculate. Margin: Entire. Texture, upper and lower surfaces: Smooth, glabrous. Color, upper surface: Close to 144B and 143A. Color, lower surface: Close to 142A and 143A.

*Peduncles*.—Length: About 1.7 cm. Diameter: About 1.5 mm. Angle: Upright. Strength: Strong. Texture: Smooth, glabrous. Color: Close to 143C.

*Pedicels*.—Length: About 7.6 mm. Diameter: About 1 mm. Angle: About 30° from peduncle axis. Strength: Strong, Texture: Smooth, glabrous. Color: Close to 145A.

*Reproductive organs*.—Stamens: Quantity per flower: Typically five. Filament length: About 7.6 mm. Filament color: Close to 157A. Anther shape: Oblong. Anther length: About 1.9 mm. Anther color: Close to 9B. Pollen amount: Abundant. Pollen color: Close to 14B. Pistils: Quantity per flower: One. Pistil length: About 3.3 mm. Stigma shape: Bi-parted. Stigma color: Close to 3C. Style length: About 1.6 mm. Style color: Close to 149C. Ovary color: Close to 144B.

*Seeds and fruits*.—Seed and fruit development have not been observed on plants of the new *Phlox*.

Disease & pest resistance: Plants of the new *Phlox* have not been noted to be resistant to pathogens and pests common to *Phlox* plants.

Temperature tolerance: Plants of the new *Phlox* have been observed to tolerate temperatures ranging from about 5° C. to about 40° C.

It is claimed:

1. A new and distinct *Phlox* plant named 'Duephloimdebu' as illustrated and described.

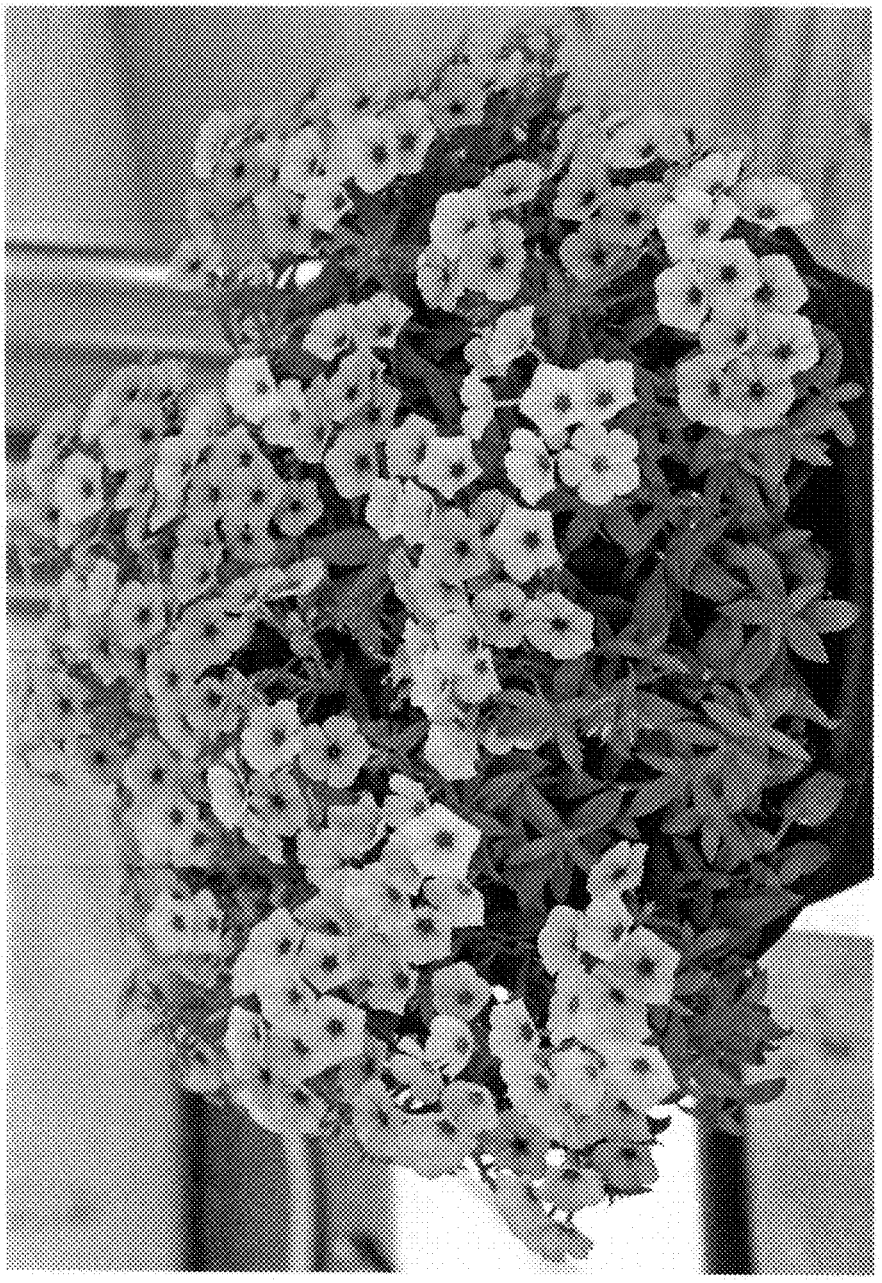

* * * * *